United States Patent [19]

Urata et al.

[11] Patent Number: 4,735,900

[45] Date of Patent: Apr. 5, 1988

[54] ENZYME PREPARATION FOR INTERESTERIFICATION

[75] Inventors: Kouichi Urata; Yoshitaka Hirota; Hideki Yokomichi, all of Ibaraki; Yoshiharu Kawahara, Sawara, all of Japan

[73] Assignee: Kao Corporation, Tokyo, Japan

[21] Appl. No.: 808,409

[22] Filed: Dec. 12, 1985

[30] Foreign Application Priority Data

Dec. 21, 1984 [JP] Japan ................... 59-270316
Dec. 21, 1984 [JP] Japan ................... 59-270317

[51] Int. Cl.$^4$ .......................... C12P 7/64; C12N 9/20
[52] U.S. Cl. ..................................... 435/134; 435/198
[58] Field of Search ........................... 435/134, 198

[56] References Cited

U.S. PATENT DOCUMENTS 4,268,527  5/1981  Matsuo et al. ............. 435/134 X
4,472,503  9/1984  Matsuo et al. ............. 435/198 X Primary Examiner—Lionel M. Shapiro
Attorney, Agent, or Firm—Flynn, Thiel, Boutell & Tanis

[57] ABSTRACT

The interesterification between an oil or fat and a fatty acid or between an oil or fat and another is improved by use of a lipase preparation in which lipase has been activated by water or a lower, dihydric or trihydric alcohol.

9 Claims, No Drawings

ENZYME PREPARATION FOR INTERESTERIFICATION

The present invention relates to a process for activating an enzyme in an enzyme preparation useful for the decomposition or modification of oils and fats.

Intensive investigations are made in this technical field for the purpose of producing oil and fat products having a high value added by modifying vegetable or animal oils and fats occurring in abundance in nature.

For example, various processes have been proposed recently for producing a substitute for cacao butter which is used as a starting material for chocolates by an enzymatic interesterification reaction of an oil or fat so as to add a high value to the oil or fat, taking advantage of the specific properties of lipase.

Lipase exhibits catalytic effects not only on the hydrolysis of oils and fats but also on an esterforming reaction which is a reverse reaction of the hydrolysis reaction when the conditions are selected suitably. The interesterification reaction which belongs to the esterforming reactions and which is one of important techniques of modifying oils and fats can be carried out efficiently, taking advantage of these characteristic properties of lipase.

However, quite important problems are posed in the development of enzymatic techniques that the activity of the enzyme must be exhibited as far as possible and that an excellent process for producing an active enzyme preparation must be developed.

To solve these problems, the following processes have been proposed: for example, a process wherein a very small amount of water is used as an enzyme activator so as to obtain the interesterification activity (see the specification of Japanese Patent Laid-Open No. 104506/1977) and a process wherein a lower dihydric or trihydric alcohol (such as a polyhydric alcohol, e.g. glycerol) is used (see the specifications of Japanese Patent Publication No. 6480/1982 and Laid-Open No. 78496/1982).

For the production of active enzyme preparations, processes have been proposed wherein a carrier is dispersed in an aqueous lipase solution to adsorb lipase or a lipase-containing substance on the carrier and then the carrier is dried to obtain an enzyme preparation having a given water content (see, for example, the specifications of Japanese Patent Laid-Open Nos. 127087/1981 and 48006/1983).

However, these known processes have defects which will be described below and, therefore, they cannot be employed as satisfactory processes to be carried out on an industrial scale.

Namely, it has been known that when a very small amount of water is used as the enzyme activator in the interesterification reaction of an oil or fat, the hydrolysis reaction of the oil or fat occurs in addition to the intended interesterification reaction to reduce the yield of the interesterified product [refer to, for example, Journal of American Oil Chemist's Society, 60, 291–294 (1983)]. After investigations, the inventors found that when a lower polyhydric alcohol such as glycerol is used in place of water having the above-mentioned defects, the interesterification reaction proceeds only very slowly and it takes nearly one week for obtaining an intended yield, though an effect of controlling the hydrolysis reaction can be obtained to a certain extent.

By-products formed by the hydrolysis reaction of the oils and fats damage the properties of the oils and fats obtained by the interesterification reaction to inhibit the production of oil and fat products having a high quality or a given quality. Further, in order to maintain the intended quality, these by-products must be removed and, therefore, an additional treatment step such as separation and purification is necessitated. This invites complication of the steps to inhibit the practical performance of the process on an industrial scale and to cause a change of the composition of the oil or fat in the treatment step.

Thus, the conventional processes wherein the enzyme activator is used are yet unsatisfactory. Recently, it has been proposed to use (1) a surfactant (emulsifier) as an enzyme catalyst which overcomes several defects of the enzyme activator and which inhibits the hydrolysis reaction to carry out the interesterification efficiently (see the specification of Japanese Patent Laid-Open No. 198798/1982), or (2) a highly water-absorptive resin (see the specification of Japanese Patent Laid-Open No. 116689/1983). However, even when these enzyme catalysts are used according to said processes, the hydrolysis reaction cannot be inhibited sufficiently, the emulsifier remains in the interesterified fat or impurities (such as monomers) might exude from the highly water-absorptive resin as shown in examples given therein. Thus, these processes are similarly unsatisfactory.

In the second process for producing the active enzyme preparation, it takes a long time for the drying treatment so as to obtain the enzymatic activity and the drying rate must be strictly controlled so as to obtain an optimum enzymatic activity. In addition, the enzymatic activity is lost in the course of the drying treatment conducted over a long period of time. Thus, also this process is unsatisfactory for the performance on an industrial scale because it requires a complicated operation and much labor.

After intensive investigations made under these circumstances for the purpose of finding an enzyme catalyst which accelerates only the intended interesterification reaction and which markedly inhibits side reactions, the inventors found previously a process for producing an enzyme (lipase) preparation by a new, easy enzyme activation technique and applied for patent (Japanese Patent Application No. 110333/1984).

However, the interesterification reaction of the oils and fats with these enzyme preparations having a high interesterification activity still have the following problems: it takes a long time in carrying out the conventional processes on an industrial scale and the interesterification must be effected efficiently, since the enzyme is expensive. To solve these problems, it is possible, for example, to add an enzyme-activator such as water in a large amount so as to reduce the reaction time by increasing the reaction rate. However, side reactions such as hydrolysis of the oil or fat are caused, in addition to the intended reaction, to reduce the productivity and quality of the intended oil or fat seriously. Further, for controlling the side reactions, complicated operations such as a dehydration treatment are inevitable to thereby complicate the steps and to make the performance of the process on an industrial scale difficult. Though there might be proposed another idea, i.e. the reduction in the amount of the expensive enzyme, a mere reduction invites a reduction in the reaction rate and lowering of the quality of the intended oil or fat.

Thus, this idea cannot be realized easily on an industrial scale.

The interesterification reaction of oils and fats has been carried out by a chemical process wherein an alkaline substance such as an alkali metal alcoholate, alkali metal or alkali metal hydroxide is used as a catalyst. However, according to this process, no specificity can be obtained with respect to the position of a fatty acid in the obtained oil or fat, since the position of the fatty acid to be exchanged in the oil or fat is indiscriminate. Namely, the conventional interesterification process according to the chemical technique has a defect that the position of the fatty acid to be exchanged cannot be specified.

Recently, processes for the interesterification of oils and fats wherein the position can be specified have been developed in place of the conventional non-selective process.

A typical example of these processes comprises an interesterification of oils and fats with lipase which is an enzyme capable of hydrolyzing the oils and fats (refer to the specification of Japanese Patent Laid-Open No. 104506/1977).

In this process, it is an indispensable requisite that water be present in the reaction system so as to activate the lipase. Though the amount of water is as small as only 0.2 to 1.0%, by-production of a diglyceride, etc. by the hydrolysis of the oil or fat and reduction in the yield of the interesterified product are unavoidable in the presence of even the small amount of water, since lipase is essentially an enzyme which hydrolyzes the oil or fat in the presence of water.

The by-products such as the diglyceride which damage the intended properties of the interesterified oil or fat seriously must be removed by complicated separation and purification steps. Thus, the known processes are yet unsatisfactory.

Under these circumstances, various processes have been proposed for effecting the interesterification efficiently by overcoming the defects of the known processes and inhibiting the hydrolysis of the oil or fat. Examples of them are as follows:

(a) a process for the interesterification of oils and fats wherein a lower polyhydric alcohol is used in place of water as the lipase activator to inhibit the hydrolysis of the oil or fat (see the specification of Japanese Patent Publication No. 6480/1982), (b) a process developed on the basis of the fact that the interesterification reaction of an oil or fat proceeds on the interface in a heterogeneous reaction system comprising an oil and water in which lipase is soluble, which process comprises adding a surfactant (emulsifier) to the heterogeneous reaction system so as to contact the oil or fat with lipase on the interface efficiently (see the specification of Japanese Patent Laid-Open No. 198798/1982), (c) a process wherein the amount of water is controlled with a water-absorptive resin which absorbs several hundred parts by weight of water per part by weight thereof (see the specification of Japanese Patent Laid-Open No. 116689/1983), (d) a process wherein the interesterification reaction of an oil or fat is carried out highly homogeneously by using a lower alcohol ester of a fatty acid having a low melting point in place of the fatty acid per se having a high melting point (see the specification of Japanese Patent Publication No. 27159/1982), and (e) a process wherein the interesterification rate of an oil or fat is increased and the hydrolysis of the oil or fat is inhibited by controlling the amount of water in the reaction system by drying and circulating a solvent vapor. See the Japanese patent early publication No. 500638/83.

However, these known processes are yet unsatisfactory, since they have some defects. The detailed description will be made on these defects.

The process (a) is characterized in that a lower polyhydric alcohol such as glycerol is used in place of water as the lipase activator. However, according to the results of the inventors' investigations, the interesterification reaction proceeds only very slowly and it takes nearly one week for obtaining an intended yield, though an effect of controlling the hydrolysis reaction can be obtained to a certain extent.

It was reported that, in the process (b), the oil or fat is contacted effectively with lipase on the interface between the oil or fat layer and the aqueous layer in the presence of the surfactant (emulsifier) and, accordingly, the interesterification reaction proceeds selectively. More particularly, it is believed that a condition suitable for the formation of a complex of lipase and the substrate is realized by the formation of an inverse micelle on the surface of the enzyme protein and, as a result, the interesterification reaction is accelerated.

However, as disclosed in examples given in the specification of said Japanese Patent Laid-Open No. 198798/1982, the hydrolysis reaction is inhibited only insufficiently and the surfactant (emulsifier) remains in the interesterified product to damage the physical properties of the oil or fat. The removal of the surfactant (emulsifier) from the obtained product requires, however, complicated treatment steps and the performance of said process on an industrial scale is made difficult.

In also the process (c), the hydrolysis of the oil or fat cannot be inhibited sufficiently and a starting monomer contained in the resin as an impurity might exude into the oil or fat. Further, according to the inventors' tests, when the water-absorptive resins are contacted with water, they are swollen and deposited on the walls of the reaction vessel. This invites a loss of lipase to be recovered for reuse.

In the process (d), a fatty acid ester must be prepared prior to the interesterification of the oil or fat and, therefore, this process requires complicated steps.

In the process (d), lipase might be deactivated by a large amount of water while water is removed from the reaction system by the circulation and drying of the solvent. This is a serious defect in the recovery and reuse of lipase.

Thus, these known processes have defects and, therefore, they cannot be employed as satisfactory processes to be carried out on an industrial scale.

Though various processes have been proposed in addition to the above-mentioned known processes, no process capable of inhibiting the hydrolysis of the oil or fat and effecting only the interesterification has been established yet.

After intensive investigations made under these circumstances for the purpose of developing a process capable of carrying out only the interesterification efficiently while the hydrolysis of the oil or fat is inhibited, the inventors found previously that said purpose can be attained by using an enzyme (lipase) preparation obtained by a new, easy lipase activation process and applied for patent (Japanese Patent Application No. 110334/1984).

However, the interesterification reaction of the oils and fats with the above-mentioned lipase preparations still have defects that it takes a long reaction time. The necessity of the long reaction time is disadvantageous in carrying out the reaction on an industrial scale and, in addition, lipase might be deteriorated in the course of its use as the enzyme catalyst for a long period of time.

SUMMARY OF THE INVENTION

The invention provides an improved process for interesterification between an oil or fat and a fatty acid or between an oil or fat and another and then a lipase preparation.

The lipase preparation is produced by mixing lipase, a lipase activator and a carrier, adding an oil or fat to the mixture, reacting the reaction mixture to decompose the oil and fat, then removing away the oil and fat component from the reaction product to separate the lipase preparation and wetting the lipase preparation with a lipase activator to activate the lipase.

After intensive investigations made for the purpose of developing a process wherein the side reactions are inhibited remarkably, the reaction time is reduced by increasing the rate of the intended interesterification reaction and the amount of the enzyme used is reduced under the circumstances as above, the inventors have found an easy enzyme activation process effective for attaining the above-mentioned purpose. The present invention has been completed on the basis of this finding.

The present invention provides an easy process for activating an enzyme in an enzyme preparation having the interesterification activity. When the enzyme preparation activated by the process of the present invention is used for the interesterification reaction of an oil or fat, side reactions are inhibited, the intended interesterification reaction is carried out efficiently within a short period of time and the amount of the enzyme used can be reduced.

The present invention provides a process for activating lipase characterized in that a lipase preparation is subjected to a wetting treatment with a lipase activator to activate lipase in the lipase preparation prior to its use.

The lipase preparations according to the present invention include those obtained by adding an oil or fat to a mixture of a lipase activator, lipase and a carrier to react them with each other and to decompose the oil or fat and then removing the oil or fat from the decomposition product by filtration or the like, and those used at least once for the interesterification reaction.

The lipase activator to use in the invention is one or a mixture of two or more members of the group consisting of water and lower dihydric and trihydric alcohols.

Now, the detailed description will be made on the present invention. First, a mixture comprising an oil or fat, a carrier, a lipase activator (such as water or dihydric or trihydric lower alcohol) and lipase is reacted to decompose the oil or fat. Then, the remaining oil or fat is removed from the decomposition product by filtration or the like to obtain a mixture comprising lipase and the carrier (lipase preparation).

The obtained lipase preparation is used as it is or, if necessary, after washing with a solvent which does not affect the lipase activity (such as a hydrocarbon). The lipase preparation is dried and then wetted. More particularly, the lipase preparation is subjected to the wetting treatment with the lipase activator and left to stand for a given period of time prior to its use in the interesterification reaction. By the wetting treatment, the interesterification activity of the lipase preparation is further increased. The lipase preparation thus activated can be used for the interesterification reaction.

The lipase preparations used in the present invention are produced under the following conditions: Lipase used has preferably a practical selectivity such as a selectivity towards the position to be bonded with the glyceride or towards the variety of the fatty acid, since when its selectivity is poor in the interesterification, special superiority to the conventional interesterification reaction carried out in the presence of an alkali metal catalyst or the like cannot be obtained. Examples of the lipase having excellent selectivity towards the position include one produced by Rhizopus, Aspergillus, Candida and Mucor microorganisms and pancreas lipase. Many of them are easily available on the market. In case the fatty acid groups in positions 1 and 3 of the glyceride are to be interesterified specifically, a lipase having properties suitable for this purpose such as one produced by *Rhizopus delemar, Rhizopus japonicus* or *Mucor japonicus* is used.

Preferred examples of the lipase activators include water and lower dihydric and trihydric alcohols. Among them, water and glycerol are particularly effective. These lipase activators may be used either alone or in the form of a mixture of two or more of them.

The carrier is selected from known ones which are insoluble in the reaction system used in the production of the lipase preparation of the present invention and which do not affect the lipase activity, such as Celite, diatomaceous earth, kaolinite, pearlite, silica gel, glass fibers, active carbon, cellulose powder and calcium carbonate. The carrier may be in various forms such as powder, granule or fiber.

The oils and fats used in the present invention include general vegetable and animal oils and fats, processed ones and mixtures of them. Examples of them include soybean oil, cotton seed oil, rape oil, olive oil, corn oil, coconut oil, safflower oil, beef tallow, lard and fish oil. When the lipase preparation obtained in the process of the present invention is used in the interesterification reaction carried out for the production of a cacao butter substitute, there may be used an oil or fat containing an oleic acid group in position 2 of the glyceride, such as palm oil, olive oil, tsubaki oil, sasanqua oil, sal fat, illippe butter, kokum butter, shea butter, mowrah fat, phulwara butter, Borneo tallow and fractionated oils obtained from them.

Now, the description will be made on the conditions for producing the lipase preparation used in the present invention. 0.01 to 10 parts by weight of commercially available lipase, 0.1 to 20 parts by weight of water or a lower dihydric or trihydric alcohol and 1 to 50 parts by weight of a carrier are added to 100 parts by weight of the oil or fat and the mixture is stirred at 20° to 80° C. for 1 to 24 h to decompose the oil or fat. The order of the addition of them is not particularly limited. The decomposition temperature for the oil or fat is selected suitably for the action of the lipase within the above-mentioned range.

Then, the oil or fat is removed from the decomposition product by filtration or the like to obtain the lipase preparation having a high interesterification activity. If necessary, the lipase preparation may be washed with an inert organic solvent which does not damage the activity of the lipase, such as a hydrocarbon, e.g. petroleum benzine, n-hexane and petroleum ether, and then dried to obtain the intended product.

The lipase preparation obtained as above is subjected to the wetting treatment with the lipase activator prior to its use in the interesterification reaction of an oil or fat. The wetting treatment conditions are as follows:

In the process of the present invention, the lipase preparation obtained by the above-mentioned process is contained with a lipase activator to be used in the interesterification reaction to activate the lipase contained in the lipase preparation prior to its use in the interesterification reaction of the oil or fat. The lipase thus activated is added to the reaction system.

The lipase activators used in the wetting treatment according to the present invention are the same as those used in the interesterification reaction of the oil or fat. More specifically, water or a lower dihydric or trihydric alcohol is preferred. Among them, water or glycerol is particularly effective. The lipase activator such as water or the lower dihydric or trihydric alcohol used in the production of the lipase preparation may be the same or different from that used in the wetting treatment.

The lipase activator is used preferably in an amount of 0.01 to 30 wt. % based on the lipase including the total amount of the carrier(s). These lipase activators may be used either alone or in the form of a mixture of two or more of them in any proportion.

The wetting treatment is conducted preferably at a temperature selected suitably within a temperature range in which the lipase activity is not inhibited. Usually, sufficient activation can be attained by the wetting treatment carried out around a room temperature (25° C.).

Though the wetting treatment time varies depending on the variety and amount of the lipase activator used and the treatment temperature, this treatment is effected desirably by leaving the mixture to stand for at least several hours.

The process of the present invention is characterized in that it is effective for the activation of not only the above-mentioned lipase preparation but also a lipase preparation which has been used in the interesterification reaction one or more times to exhibit also a high lipase activity.

As described above in detail, the lipase preparation having a high activity can be obtained by the wetting treatment.

According to the process of the present invention for activating the lipase preparation having an interesterification activity, a side reaction (hydrolysis) is controlled and only the interesterification reaction is carried out efficiently. In addition, the reaction time can be reduced remarkably as compared with that required in the known processes as will be apparent from the following examples and comparative examples. Another advantage of the process of the present invention is that the amount of lipase used may be reduced remarkably. Therefore, the process of the present invention can be carried out easily on an industrial scale to exhibit significant economical effects (such as the reduction of the reaction time and the amount of lipase used).

The present invention provides a process for the interesterification of oils and fats characterized in that an interesterification reaction between an oil or fat and a fatty acid or between oils or fats is carried out in the presence of a lipase preparation pretreated by wetting with a lipase activator.

More particularly, according to the present invention lipase in the lipase preparation is activated by pretreating it by wetting with the same lipase activators as those used in the interesterification reaction (such as water or lower dihydric or trihydric alcohol) prior to the interesterification of the oils or fats and then the preparation containing lipase thus activated is added to a reaction mixture to effect the interesterification reaction of the oils or fats. By this process, the reaction time can be reduced remarkably and the hydrolysis of the oils and fats can be controlled.

The lipase position used once in the interesterification reaction of an oil or fat may be used in addition to the above-mentioned lipase preparations. The lipase preparation separated from the interesterification reaction mixture by filtration or the like is used as it is or, if necessary, after washing with a solvent which does not affect the lipase activity (such as a hydrocarbon). The lipase preparation is dried and then subjected to the wetting treatment. The lipase activator (such as water or a lower dihydric or trihydric alcohol) as used in the interesterification reaction of the oil or fat is added to the lipase preparation obtained as above. The obtained mixture is subjected to the wetting treatment by stirring or leaving to stand and then added to the reaction mixture comprising the oil or fat, a fatty acid and a solvent (hydrocarbon) or to a mixture of oils or fats and a solvent (hydrocarbon) to carry out the interesterification reaction of the oils or fats.

The fatty acid and small amounts of the monoglyceride and diglyceride are removed from the interesterification reaction product by known separation or purification techniques such as liquid-liquid extraction, alkali neutralization, vacuum or molecular distillation or a combination of these techniques to obtain the refined product.

Though the oil or fat used in the production of the lipase preparation and that to be interesterified may be selected independently from each other, it is desirable that the composition of the former oil or fat is the same as or close to that of the latter.

The interesterification of the oil or fat is conducted by reacting it with a fatty acid or with another oil or fat.

The fatty acids used include straight-chain fatty acids having 8 to 22 carbon atoms and occurring in nature, such as palmitic, stearic or oleic acid.

In the interesterification, alcohol esters of fatty acids may be used in addition to the above-mentioned fatty acids. These esters are formed from said fatty acids (straight-chain fatty acids having 8 to 22 carbon atoms) and straight-chain saturated monohydric alcohols having 1 to 6 carbon atoms. Examples of them include methyl palmitate, ethyl palmitate, methyl stearate and ethyl stearate. The oil or fat is selected according to the purpose from the above-mentioned oils and fats (ordinary vegetable and animal oils and fats, processed oils and fats and mixtures of them).

The solvents used in the interesterification reaction to be carried out in a solvent according to the present invention include organic solvents inert to lipase, such as n-hexane, technical grade hexane, petroleum ether and petroleum benzin. The solvents used in the production of the lipase preparation may be the same as those used in the interesterification.

The lipase preparation obtained as above is subjected to the wetting treatment with the lipase activator. With this wet lipase preparation, the interesterification reaction is carried out as follows: 100 parts by weight of the oil or fat is mixed with 25 to 300 parts by weight of a fatty acid (or an alcohol ester of the fatty acid or another oil or fat), 0.01 to 100 parts by weight of a product [obtained by the wetting treatment of 0.1 to 100 parts by weight of the lipase preparation (comprising 0.01 to 10 parts by weight of lipase and the balance of the carrier) with 0.01 to 10 parts by weight of the lipase activator (water or a lower dihydric or trihydric alcohol) at a temperature at which the lipase activity is not damaged (preferably 25° to 30° C.) for at least one hour (preferably at least several hours)] and, if necessary, up to 1000 parts by weight of the inert organic solvent. The mixture is stirred at 20° to 80° C.

The interesterification reaction temperature is selected suitably for the lipase activity within the above-mentioned temperature range according to the present invention. The above-mentioned lipase preparation may be replaced with one used at least once in the interesterification of an oil or fat. In this case, it is subjected to the wetting treatment in the same manner as above and then used in the interesterification.

After completion of the interesterification reaction, the fatty acid and a small amount of the monoglyceride and diglyceride can be removed easily by conventional separation or purification techniques such as liquid-liquid extraction, alkali neutralization, vacuum or molecular distillation or a combination of these techniques to obtain the refined product.

The effects and advantages of the present invention reside in that the lipase preparation having a high interesterification activity obtained by an easy process is subjected to the wetting treatment to further improve its activity prior to its use in the interesterification reaction so that only the intended interesterification reaction is carried out efficiently within a short period of time while the hydrolysis of the oil or fat is inhibited. An remarkably high productivity can be obtained by this process.

Another effect of the present invention is that lipase is substantially not deactivated in the course of the reaction, since the reaction time is reduced. Accordingly, the lipase preparation recovered after completion of the reaction can be used effectively again. When the process of the invention is conducted on an industrial scale, a great economical advantage can be obtained.

When lipase having a selectivity toward the position is used in the interesterification reaction according to the present invention, for example, an expensive cacao butter substitute can be produced effectively from inexpensive palm oil.

The following referential examples, examples and comparative examples will further illustrate the present invention.

REFERENTIAL EXAMPLE (Production of Lipase Preparation)

100 g of a soft fraction of palm oil, 10 g of Celite, 1.0 g of ion-exchanged water and 8.7 g of commercially available lipase [lipase produced by Rhizopus delemar and having an activity of 6000 lipase unit/g; a product of Tanabe Seiyaku Co., Ltd.] were stirred together in a closed vessel at 40° C. for 18 h to carry out the enzymatic reaction (hydrolysis).

After completion of the reaction, an insoluble matter (a mixture of Celite and lipase) was separated by filtration. The residue was washed with 5 ml of n-hexane three times to remove the oil thoroughly. After drying at 20° to 30° C. under reduced pressure for 1 h, a lipase preparation was obtained.

EXAMPLE 1

Interesterification Reaction With the Lipase Preparation (With Wetting Treatment)

0.015 g of ion-exchanged water was added to the lipase preparation obtained in the above referential example (comprising 0.87 g of lipase and 1.00 g of Celite) to effect the wetting treatment in a closed vessel for 24 h. The obtained product was stirred together with 10 g of a medium melting fraction of palm oil (having an iodine value of 34 and diglyceride content of 1%), 10 g of stearic acid and 40 ml of n-hexane at 40° C. in a closed vessel for one day to carry out the enzymatic reaction (interesterification reaction). After completion of the reaction, insoluble substances such as the lipase preparation were removed by filtration and n-hexane was distilled off from the filtrate under reduced pressure. From the obtained interesterified oil, diglyceride and triglyceride fractions were taken out by means of column chromatography. The stearic acid content of the triglyceride fraction was determined by means of gas chromatography. The stearic acid and diglyceride contents thus determined are shown in Table 1.

COMPARATIVE EXAMPLE 1

Interestification Reaction With the Lipase Preparation (Without Wetting Treatment)

1.87 g of the lipase preparation obtained in the above referential example, 10 g of a medium melting fraction of palm oil, 10 g of stearic acid, 0.015 g of ion-exchanged water and 40 ml of n-hexane were stirred together at 40° C. in a closed vessel for two days to carry out the enzymatic reaction (interesterification reaction). After completion of the reaction, the stearic acid and diglyceride contents of the resulting triglyceride were determined in the same manner as in Example 1 to obtain the results shown in Table 1.

COMPARATIVE EXAMPLE 2

Interesterification Reaction Without Lipase Preparation (With Wetting Treatment)

0.87 g of the same, commercially available lipase as in the above referential example was mixed with 1.0 g of Celite. 0.015 g of water was added to the mixture and the wetting treatment was conducted in a closed vessel for 24 h. The whole amount of the obtained product was stirred together with 10 g of a medium melting fraction of palm oil, 10 g of stearic acid and 40 ml of n-hexane at 40° C. in a closed vessel for three days to carry out the enzymatic reaction (interesterification reaction). After completion of the reaction, the stearic acid and diglyceride contents of the obtained triglyceride were determined in the same manner as in Example 1 to obtain the results shown in Table 1.

COMPARATIVE EXAMPLE 3

Interesterification Reaction Without Lipase Preparation (Without Wetting Treatment)

0.87 g of the same, commercially available lipase as in the above referential example was stirred together with 1.0 g of Celite, 10 g of a medium melting fraction of palm oil, 10 g of stearic acid, 0.015 g of ion-exchanged water and 40 ml of n-hexane at 40° C. in a closed vessel for 4 days to carry out the enzymatic reaction (interesterification reaction). After completion of the reaction, the stearic acid and diglyceride contents of the obtained triglyceride were determined in the same manner as in Example 1 to obtain the results shown in Table 1.

TABLE 1

| Results of the interesterification reaction | | | | |
|---|---|---|---|---|
| | Interesterification conditions | | | |
| | Water content* | Wetting time | Reaction time | Stearic acid content | Diglyceride content |
| Lipase preparation (Example 1) | 0.15% | 24 h | 1 day | 38.6% | 4.6% |
| Lipase preparation (Comparative Example 1) | 0.15% | 0 | 2 days | 37.9% | 4.4% |
| Commercially available lipase preparation per se (Comparative Example 2) | 0.15% | 24 h | 3 days | 28.8% | 4.7% |
| Commercially available lipase preparation per se (Comparative Example 3) | 0.15% | 0 | 4 days | 19.0% | 4.7% |

Note
*based on the oil

EXAMPLE 2

Interesterification Reaction With the Lipase Preparation (Reduction in the Amount of Lipase By Wetting Treatment)

The interesterification wa carried out with the lipase preparation obtained in the referential example under the same conditions as in Example 1, while the amount of lipase was varied in the range of 100 to 390 lipase unit/g-oil. For comparison, the interesterification was carried out under the same conditions as above but without the wetting treatment. The reaction product was treated and analyzed in the same manner as in Example 1 to obtain the results shown in Table 2.

TABLE 2

| Reduction in the amount of lipase** | | |
|---|---|---|
| | Stearic acid content (%) | |
| Amount of lipase used (lipase unit/g-oil) | With wetting treatment* | Without wetting treatment |
| 100 | 41.2 | 31.6 |
| 130 | 40.6 | 33.5 |
| 260 | 40.8 | 38.8 |
| 390 | 41.2 | 41.2 |

Note
*wetting treatment; 30° C., 24 h
**reaction conditions: water content: 0.15% based on the oil, 43° C., 3 days.

EXAMPLE 3

Interesterification Reaction With the Lipase Preparation Used Repeatedly (With Wetting Treatment)

0.3 g of ion-exchanged water was added to 18.7 g of the lipase preparation obtained in the above referential example and the wetting treatment was carried out at 30° C. in a closed vessel for 24 h. A mixture comprising the whole amount of the lipase preparation obtained by the wetting treatment, 200 g of a medium melting fraction of palm oil, 200 g of stearic acid and 800 ml of n-hexane was stirred at 40° C. in the closed vessel to carry out the enzymatic reaction (interesterification reaction). After completion of the reaction, insoluble substances such as the lipase preparation were removed by filtration and the filtrate was taken. n-Hexane was distilled off from the filtrate under reduced pressure to obtain an interesterified oil. The stearic acid content of the interesterified oil was determined in the same manner as in Example 1. The lipase preparation separated by the filtration was dried at 20° C. under reduced pressure for 1 h. Then 0.3 g of ion-exchanged water was added thereto and the mixture was subjected again to the same wetting treatment as above and then to the interesterification reaction under the same conditions as above. The stearic acid content of the obtained interesterified oil was determined in the same manner as above.

The lipase preparation was recovered and treated in the same manner as above before subjected to the wetting treatment and used in the interesterification reaction. The results are shown in Table 3.

TABLE 3

| Results obtained with the lipase preparation used repeatedly | | | | |
|---|---|---|---|---|
| Number of times of reaction | 1 | 2 | 3 | 4 |
| Stearic acid content (%) | 38.0 | 38.2 | 38.3 | 37.1 |

The embodiments of the invention in which an exclusive pdrivilege or property is claimed are defined as follows:

1. A process for preparing a lipase preparation, which comprises the steps of:
    enzymatically reacting a lipase with an enzymatically decomposable oil or fat, in the presence of a first lipase activator and a carrier, whereby to decompose said oil or fat; then separating from the reaction mixture the residue of said oil or fat and recovering an intermediate lipase preparation consisting essentially of said lipase and said carrier;
    then wetting said intermediate lipase preparation with a second lipase activator, in the absence of fat or oil, to improve the activity of said lipase and form a final lipase preparation consisting essentially of said lipase and said carrier and which exhibits a high lipase activity.

2. A process as claimed in claim 1 in which said lipase activators are selected from the group consisting of water, lower dihydric alcohols and lower trihydric alcohols, and in said enzymatic reaction step, from 0.01 to 10 parts by weight of said lipase, from 0.1 to 20 parts by weight of said lipase activator and from 1 to 50 parts by weight of a carrier are added to 100 parts by weight of said oil or fat and the reaction mixture is stirred at 20° to 80° C., for from 1 to 24 hours, to decompose said oil or fat.

3. A process as claimed in claim 2 in which said first second lipase activators are the same.

4. A process as claimed in claim 2 in which said first and second lipase activators are water.

5. A process as claimed in claim 2 in which, in said wetting step, from 0.01 to 30 wt. % of said second lipase activator, based on the weight of said intermediate lipase preparation, is added to and mixed with said intermediate lipase preparation, at from 25° to 30° C., for at least one hour, in order to activate said lipase.

6. A process as claimed in claim 1, in which said lipase activator is water, a lower, dihydric or trihydric alcohol or a mixture thereof.

7. A lipase preparation which has been obtained by the process as claimed in claim 1.

8. In a process for an interesterification reaction between an oil or fat and a fatty acid or between two different oils or fats in the presence of a lipase preparation, the improvement which comprises using the lipase preparation as defined in claim 7.

9. In a process for an interesterification reaction between an oil or fat and a fatty acid or between two different oil or fats in the presence of a lipase preparation, the improvement which comprises using the lipase preparation as defined in claim 7 and which has previously been used in another interesterification reaction.

* * * * *

UNITED STATES PATENT AND TRADEMARK OFFICE
CERTIFICATE OF CORRECTION

PATENT NO. : 4 735 900

DATED : April 5, 1988

INVENTOR(S) : Kouichi URATA et al

It is certified that error appears in the above-identified patent and that said Letters Patent is hereby corrected as shown below:

Column 13, Line 4; Before "second" insert ---and---.

Signed and Sealed this

Twenty-fifth Day of October, 1988

Attest:

DONALD J. QUIGG

*Attesting Officer*     *Commissioner of Patents and Trademarks*